US005398691A

United States Patent [19]
Martin et al.

[11] Patent Number: 5,398,691
[45] Date of Patent: Mar. 21, 1995

[54] METHOD AND APPARATUS FOR THREE-DIMENSIONAL TRANSLUMENAL ULTRASONIC IMAGING

[75] Inventors: Roy W. Martin, Redmond; Ram B. Hatangadi; Gerard Bashein, both of Seattle, all of Wash.

[73] Assignee: University of Washington, Seattle, Wash.

[21] Appl. No.: 116,293

[22] Filed: Sep. 3, 1993

[51] Int. Cl.$^6$ .............................................. A61B 8/12
[52] U.S. Cl. .............................. 128/662.06; 128/653.1
[58] Field of Search .................... 128/660.08, 660.09, 128/661.01, 662.03, 662.06, 916, 653.1

[56] References Cited

U.S. PATENT DOCUMENTS

| | | | |
|---|---|---|---|
| 4,543,960 | 10/1985 | Harui et al. | 128/660 |
| 4,546,777 | 10/1985 | Groch et al. | 128/715 |
| 4,762,002 | 8/1988 | Adams | 73/625 |
| 4,849,692 | 7/1989 | Blood | 324/208 |
| 4,930,515 | 6/1990 | Terwilliger | 128/662.06 |
| 4,945,305 | 7/1990 | Blood | 324/207.17 |
| 4,967,752 | 10/1990 | Blumenthal et al. | 128/660.1 |
| 5,105,819 | 4/1992 | Wollschlager et al. | 128/662.06 |
| 5,127,409 | 7/1992 | Daigle | 128/660.07 |
| 5,131,397 | 7/1992 | Crowley | 128/662.06 |
| 5,191,890 | 3/1993 | Hileman | 128/662.06 |
| 5,215,092 | 6/1993 | Wray | 128/662.06 |
| 5,295,486 | 3/1994 | Wollschläger et al. | 128/916 |

FOREIGN PATENT DOCUMENTS

WO90/13259 10/1990 WIPO .

OTHER PUBLICATIONS

Brinkley, J. F., et al., "In vitro Evaluation of an Ultrasonic Three-Dimensional Imaging and Volume System," *Ultrasonic Imaging* 4:126–139 (1982).

King, D. L., Al-Banna, S. J., and Larach, D. R., "A New Three-Dimensional Random Scanner for Ultrasonic/Computer Graphic Imaging of the Heart,".

Martin, R. W., Bashein, G. Zimmer, R. and Sutherland, J., "An Endoscopic Micromanipulator for multiplanar Transesophageal Imaging," *Ultrasound in Med. & Biol.* 12:965–975 (1986).

Bashein, G., Sheenan, F. H. Nessly, M. L., Detmer, P. R. and Martin, R. W., "Three-dimensional transesophageal echocardiography for depiction of regional left-ventricular performance: initial results and future
(List continued on next page.)

*Primary Examiner*—George Manuel
*Attorney, Agent, or Firm*—Christensen, O'Connor, Johnson and Kindness

[57] ABSTRACT

Disclosed is an arrangement for use in transesophageal ultrasonic imaging of the heart (and other translumenal applications) in which both the position and orientation of an ultrasonic probe that generates an ultrasonic scanning pattern is determined in terms of a three-dimensional coordinate system that lies outside the patient's body and is produced by a magnetic field generator. The arrangement provides two-dimensional multi-planar scanning in which the ultrasonic scanning pattern is selectively positionable relative to rotation about two orthogonal coordinate axes that are mutually orthogonal to the longitudinal axis of the ultrasonic scanning probe. Provision is made for generating electrical signals indicative of rotational position of the scanning pattern relative to each of the two axes of rotation. The signals representative of the rotational position of the scanning pattern allow registration between the two-dimensional multi-plane ultrasonic images for purposes such as a computer generation of three-dimensional cardiac images. The ultrasonic probe also includes a flexure region for selectively positioning the probe in the esophagus or other lumen and a heart sound microphone for use in temporal registration of the ultrasonic imaging relative to one or more events in the cardiac cycle.

21 Claims, 9 Drawing Sheets

OTHER PUBLICATIONS directions," *International Journal of Cardiac Imaging* (1993).

King MD, D. L., King Jr., D. L., Yi-Ci Shao MS, M., "Three-Dimensional Spatial Registration and Interactive Display of Position and Orientation of Real-time Ultrasound Images", *J Ultrasound Med* 9:525-532 (1990).

Pandian, M. D., N. G. et al. "Three-Dimensional and Four-Dimensional Transeophageal Echocardiographic Imaging of the Heart and Aorta in Humus Using a Computed Tomographic Imaging Probe," *Echocardiography:* 9:677-687 (Nov. 1992).

Wollschlager, H., "Tee & 3-Dimensional Reconstruction," *10th Symposium of Echocardiology: 12(Jun. 23-25, 1993).*

Moritz, W. E., Medema, D. K., McCabe, D., Pearlman, A. S., "Three-Dimensional Imaging and Volume Determination Using a Series of Two-Dimensional Ultrasonic Scans", *Rijsterborgh H., ed: Echorcardiology:* 449-454 (1981).

METHOD AND APPARATUS FOR THREE-DIMENSIONAL TRANSLUMENAL ULTRASONIC IMAGING

This invention was made partly with government support under Grant RO1 HL41464 from the National Institutes of Health. The government has certain rights in this invention.

FIELD OF THE INVENTION

This invention relates, in general, to ultrasonic imaging and, more particularly, to ultrasonic imaging in which organs or tissue of a subject are scanned along a number of different scanning planes so that the tissue or organs can be viewed in different ways. As currently embodied, the invention provides for multi-planar transesophageal imaging of the heart and provides a plurality of two dimensional ultrasonic images that are referenced to a coordinate system that is fixed in space and has its origin outside the patient or subject being examined. Registration of the two-dimensional images to the fixed coordinate system allows computer graphics techniques to be used to obtain accurate three-dimensional cardiac imaging.

BACKGROUND OF THE INVENTION

Ultrasonic scanning has become accepted practice in various medical applications including research, diagnosis and patient monitoring. In the vast majority of such medical applications, a transducer produces an ultrasonic beam that is placed in close proximity with tissue or organs to be examined and the beam is mechanically or electronically swept through a fan-shaped or other scanning pattern. Reflection (backscatter) of the ultrasonic energy results in "echo" image signals that can be processed for visually displaying ultrasonically imaged tissue and organs and/or stored in digital or other format for subsequent computer or manual analyses.

Ultrasonic scanning of the heart (echocardiography) has presented special challenges and problems because of the relatively complex movement of the heart and dynamic changes in the heart's configuration that occur during the cardiac cycle. Because of such problems and others, cardiac ultrasonic scanning historically has been limited to two-dimensional imaging in which an ultrasonic transducer is positioned as accurately as possible relative to obtaining ultrasonic scanning of the heart along a desired plane. Two basic scanning techniques have been employed: transcutaneous and translumenal. In translumenal ultrasonic scanning, a probe that includes an ultrasonic transducer is passed along a patient's throat and is positioned in the esophagus (or stomach) where it is near the heart and an ultrasonic image can be obtained without interference of the lungs or ribs (which can present a problem in transcutaneous echocardiography). Because the esophagus extends downwardly along the long axis of the heart, multiple scanning points are available to thereby provide multiple ultrasonic images. Moreover, because the heart is in close proximity with the esophagus, a relatively high scanning frequency can be employed (often on the order of 5 megahertz), which results in higher image resolution than can be obtained with lower frequency transcutaneous scanning. In addition, esophageal echocardiography has become the technique of choice for patient monitoring during surgery because the ultrasonic probe is located outside the surgical field.

In recent years, a fair amount of effort has been devoted to the development of techniques and equipment for three-dimensional ultrasonic cardiac imaging. From the clinical standpoint, motivation for developing three-dimensional echocardiography includes imaging portions of the heart that might be missed in two-dimensional scanning and, in addition, providing a methodology for diagnosing and evaluating cardiac performance. Further motivation is provided because of the portability and relatively low cost associated with ultrasonic scanning. One of the most promising techniques for obtaining clinically applicable three-dimensional echocardiography is the use of computer graphics to produce a three-dimensional image of the heart on the basis of a number of transesophageal two-dimensional ultrasonic images that are taken along different cardiac planes.

Various problems are associated with attempting to construct a three-dimensional image of the heart from multiple two-dimensional ultrasonic images. The primary problem is that the spatial relationship (position and orientation) between the two-dimensional images is difficult to ascertain. Further, difficulty can be encountered in positioning an ultrasonic probe to obtain a desired two-dimensional cardiac image. In addition, it is desirable to obtain the two-dimensional images with a multi-planar ultrasonic probe, which can obtain a number of two-dimensional images from a single imaging site. Specifically, multi-planar imaging from a single imaging site is more suitable for use in patient monitoring applications and lessens the risk of esophageal irritation. Although multi-planar ultrasonic scanning probes are advantageous from the operational standpoint, difficulties are encountered relative to the size of such probes, especially for use with patients who are not sedated.

SUMMARY OF THE INVENTION

In accordance with this invention, apparatus for translumenal, multi-planar ultrasonic scanning is provided in which an ultrasonic probe that contains a transducer for generating a two-dimensional ultrasonic scanning pattern is located on the distal end of an endoscope. The ultrasonic transducer can be rotated and positioned about two coordinate axes of a coordinate system that translates and rotates in fixed relationship with the ultrasonic probe. An electromagnetic sensor is mounted at a fixed location within the ultrasonic probe. The electromagnetic sensor functions in conjunction with a magnetic field generator that is spatially separated from the ultrasonic scanning probe and establishes an electromagnetic field that defines a second coordinate system having its origin spaced apart from the ultrasonic probe. In particular, the electromagnetic sensor supplies signals representative of the position and orientation of the electromagnetic sensor in terms of the coordinate system established by the magnetic field generator. The ultrasonic probe also supplies signals representative of the rotational position of the transducer relative to each of the two coordinate axes about which the ultrasonic transducer can be rotated. Combined with the signals representing the position and orientation of the electromagnetic sensor, these signals identify the position and orientation of the two-dimensional scanning pattern produced by the ultrasonic transducer in terms of the coordinate system established by the magnetic field generator. The invention thus provides spatial registration between two-dimensional scans taken along different scanning planes.

In accordance with another aspect of the invention, the ultrasonic scanning probe includes a flexure region that is configured and arranged for flexure (induced curvature) in a single plane. Included in the endoscope is a wire or other means for establishing the degree of flexure. This feature of the invention allows the ultrasonic probe to be positioned at an advantageous scanning site and to be maintained in a stable position during a desired scanning interval.

The invention provides various other features and advantages. For example, the currently preferred embodiments of the ultrasonic probe include a microphone that supplies heart sound signals that can be used for determining the temporal relationship of two-dimensional ultrasonic images obtained with the invention relative to a detectable event that occurs during each cardiac cycle. All elements of the ultrasonic probe are configured and arranged to achieve miniaturization. Moreover, all components of the invention are selected and configured for relatively low manufacturing cost and high reliability.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
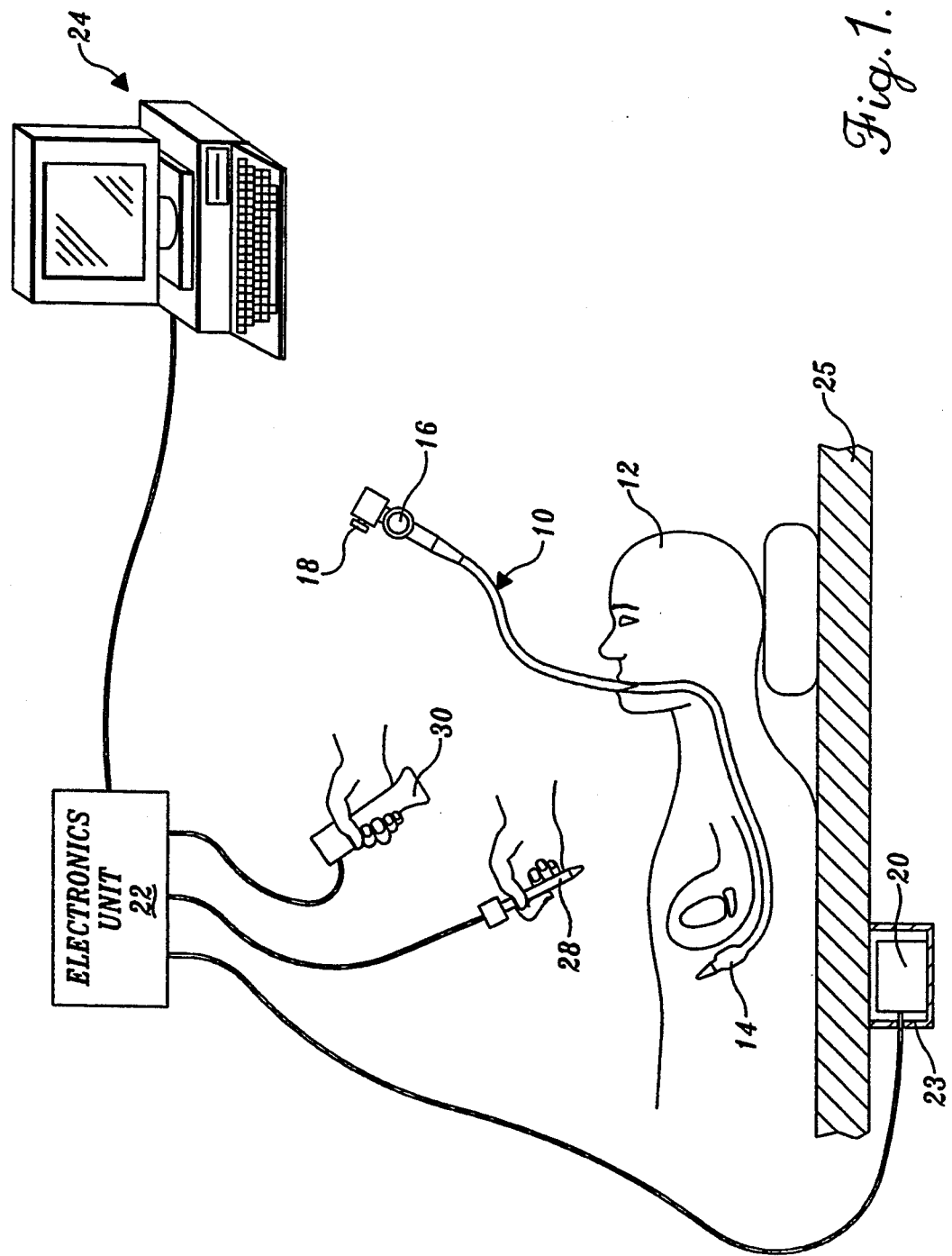
FIG. 1 diagrammatically depicts an arrangement of the invention for use in transesophageal ultrasonic scanning of patient's heart.

In the arrangement shown in FIG. 1, an ultrasonic endoscope 10 is inserted into the mouth of a patient 12 and extends downwardly through the patient's throat. Located at the distal end of ultrasonic endoscope 10 is an ultrasonic probe 14, which is positioned in the patient's esophagus (or stomach) at a position that allows two-dimensional imaging of the patient's heart. Located within ultrasonic probe 14 is a phased array or other type of ultrasonic transducer, which can be operated to produce a beam of ultrasonic energy that is swept arcuately to produce a digitally encoded signal that represents an image of the tissue and organs upon which the ultrasonic beam impinges (i.e., in FIG. 1, a two-dimensional ultrasonic image of the patient's heart). In the practice of this invention, ultrasonic probe 14 can be precisely positioned at the most advantageous location of a patient's esophagus (or stomach), which varies from person to person due to the position of the patient's heart and other factors. Moreover, as shall be described in detail, ultrasonic probe 14 of this invention includes means for rotating the transducer array (and hence the ultrasonic scanning plane) about two mutually orthogonal axes that extend outwardly from the distal end of ultrasonic endoscope 10. Two knobs 16 and 18, located on a control handle at the proximal end of ultrasonic endoscope 10 individually control rotation of the scanning pattern about the two orthogonal axes thereby allowing two-dimensional ultrasonic imaging along a plurality of selectively positioned planes that intersect the patient's heart. In most situations, positioning ultrasonic probe 14 behind the left atrium or left ventricle allows complete ultrasonic imaging of a patient's heart, i.e., provides a set of two-dimensional scans sufficient for the generation of a three-dimensional cardiac image. As also shall be described more fully, the control handle of endoscope 10 includes a control knob 19, which can be rotated to cause curvature (flexing) of the distal portion of ultrasonic probe 14. This curvature or flexing allows probe 14 to be positioned at a desired location in a patient's esophagus (or stomach) and in firm, but gentle, contact with the esophagus or stomach to thereby maintain ultrasonic probe 14 in an appropriate position throughout a desired scanning interval.

Figure 3:
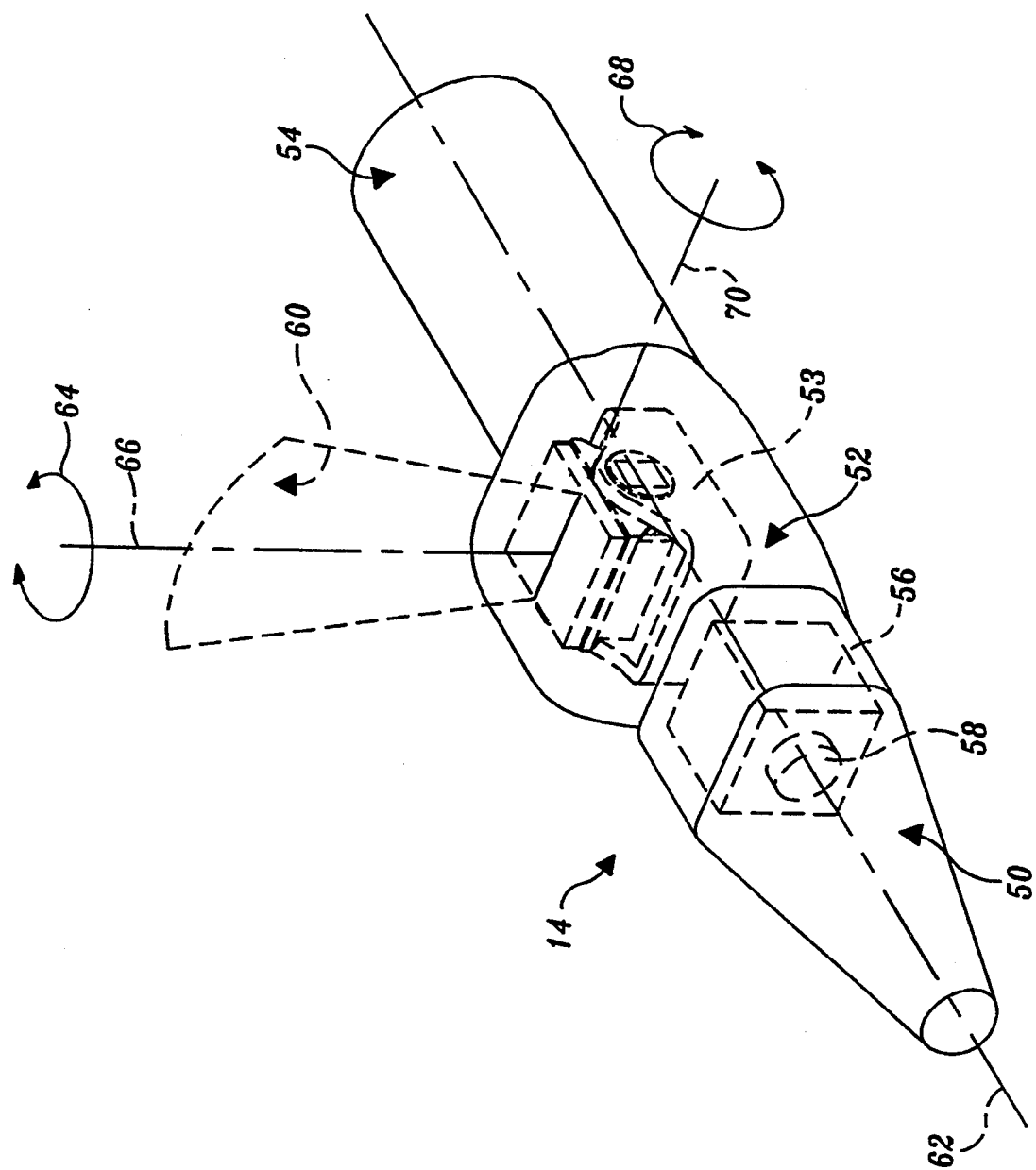
FIG. 3 is a perspective view of the ultrasonic probe of an endoscope configured in accordance with this invention and generally illustrates the manner in which the ultrasonic scanning pattern produced by the probe can be positioned in rotation about two orthogonal axes.
Figure 5:
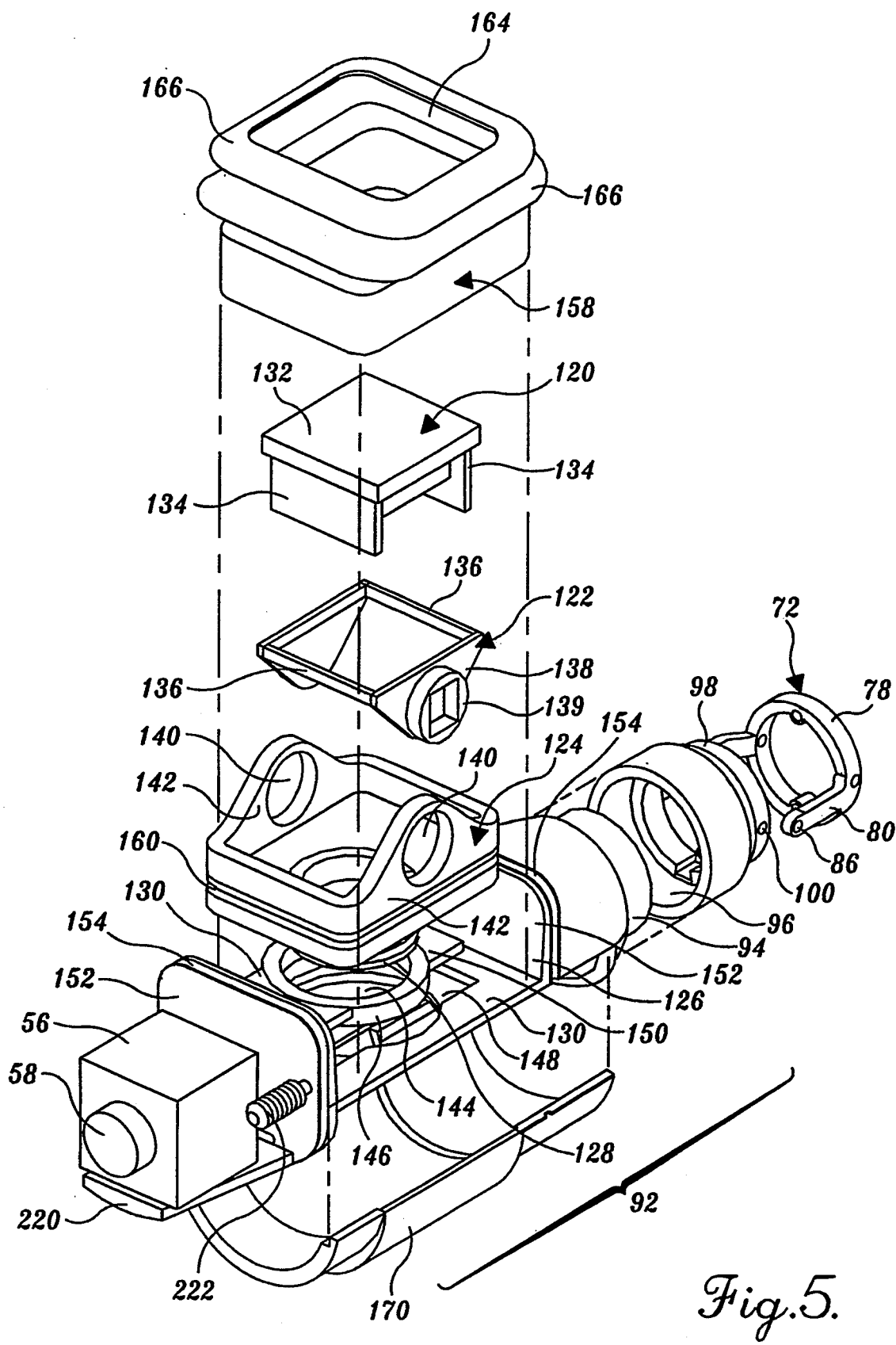
FIG. 5 is an exploded view that depicts structural components that are housed within the transducer mounting region of FIG. 4.

In accordance with another aspect of the invention, ultrasonic probe 14 also includes an electromagnetic sensor (not specifically indicated in FIG. 1; element 56 in FIGS. 3 and 5). The electromagnetic sensor operates in conjunction with a magnetic field generator 20, an electronics unit 22 and a digital signal processor that is programmed to provide a user interface (indicated in FIG. 1 by personal computer 24). In particular, the electromagnetic sensor, electronics unit 22 and the interface formed by personal computer 24 collectively form what is often called a six-degree-of-freedom measurement or tracking system. As is known in the art, such a system provides a digitally encoded signal representative of both the three-dimensional position of the electromagnetic sensor and the orientation of the sensor. With respect to the arrangement of FIG. 1, magnetic field generator 20 is positioned at a known location near patient 12 so that probe 14 (and hence the electromagnetic sensor) is immersed in the magnetic field produced by magnetic field generator 20. For example, as is shown in FIG. 1, magnetic field generator 20 can be located directly below the patient's torso in a recess 23 in an operating table 25 or other surface that supports patient 12.

Regardless of its exact position, magnetic field generator 20 includes a set of transmitter coils (not shown in FIG. 1) that sequentially generates three mutually orthogonal dipole fields, which define the coordinate axes of a fixed three-dimensional reference frame (i.e., the x, y and z axes of a Cartesian coordinate system). The electromagnetic sensor of ultrasonic probe 14 includes three miniature receiving antennas that allow the electromagnetic sensor to detect magnetic field strength in three orthogonal directions (i.e., detect magnetic field strength relative to a coordinate system that is referenced to the electromagnetic sensor and, hence, ultrasonic probe 14). Since each of the three orthogonal dipole magnetic fields supplied by magnetic field generator 20 produces three signals representative of magnetic field strength, a sequence of nine field strength signals is provided during each period of time in which magnetic field generator 20 sequentially generates three orthogonal magnetic dipole fields. (Each field strength signal includes magnetic polarity and magnitude information.)

Since each set of three magnetic field strength signals is provided relative to a three-dimensional (Cartesian) coordinate system that is established by and associated with the electromagnetic sensor (and hence probe 14), the sequence of nine magnetic field strength signals provides sufficient information for: (a) determining the location of probe 14 in terms of the three-dimensional coordinate system associated with magnetic field generator 20 (i.e., determining translation of the coordinate system associated with the magnetic sensor in terms of the three-dimensional coordinate system associated with magnetic field generator 20); and, (b) determining the orientation of ultrasonic probe 14 relative to the Cartesian coordinate system associated with magnetic field generator 20 (i.e., determining rotation of the three-dimensional coordinate system associated with the magnetic field sensor (and, hence, ultrasonic probe 14) relative to the coordinate system defined by magnetic field generator 20).

Although a sinusoidal excitation signal can be used to generate the magnetic dipole fields that are provided by magnetic field generator 20, square wave excitation preferably is employed. In particular, excitation of the magnetic field generator with a continuous sine wave results in magnetic dipole fields that exhibit a corresponding sinusoidal variation with time. Such continuously varying magnetic dipole fields induce eddy currents in electrically conducting structure objects that are subjected to the continuously varying magnetic field. The eddy currents, in turn, generate electromagnetic fields that can interfere with the magnetic dipole fields and, hence, cause errors in the position and orientation signals. On the other hand, eddy current-induced error can be eliminated or greatly reduced by employing square wave excitation signals and by measuring the orthogonal field strength components after any induced eddy currents have subsided (i.e., controlling the time at which the electromagnetic sensor produces the three orthogonal field strength signals relative to the leading and trailing edges of the square wave excitation).

A six-degree-of-freedom measurement system of the above-described type is described in further detail in U.S. Pat. Nos. 4,945,305 and 4,849,692, both of which issued to Ernest B. Blood, and are assigned to Ascension Technology Corporation of Buffington, Vt., U.S.A. In addition, six-degree-of-freedom measurement systems that are arranged and function in the above-described manner are manufactured and sold by Ascension Technology Corporation under the trademark "Flock of Birds". The Ascension Technology Corporation system used in the currently preferred practice of the invention includes a standard range transmitter unit (magnetic field generator 20 in FIG. 1), a microprocessor-based unit identified as "The Bird" (electronics unit 22 in FIG. 1) and software for programming personal computer 24 so that it provides an appropriate operator interface. In this currently preferred arrangement, electronics unit 22 processes the signals supplied by magnetic field generator 20 and the electromagnetic sensor of probe 14 and provides digitally encoded signals representative of probe position and orientation to personal computer 24 via a conventional RS-232C data bus.

The electromagnetic sensors that are used in the currently preferred embodiments of the invention are smaller than sensors conventionally employed in six-degree-of-freedom measuring systems. Specifically, the invention currently employs electromagnetic sensors developed by Ascension Technology Corporation for use in the hereinafter described probe 14 of ultrasonic endoscope 10 (and other applications calling for a miniature sensor). The currently preferred electromagnetic sensor is provided with a six-degree-of-freedom measurement system that Ascension Technology Corp. identifies as Model 6D FOB (SBIR-MOD), and is encapsulated to form a 6 mm×6 mm×9 mm rectangular solid (approximately 0.25 inch×0.25 inch×0.375 inch). In comparison, the size of the standard or more conventional Ascension Technology Corporation electromagnetic sensor is 25.4 mm×25.4 mm×20 mm (i.e., one inch×one inch×0.8 inch).

Use of a six-degree-of-freedom measurement system is advantageous in virtually all applications of the invention since it provides precise information as to the position and orientation of ultrasonic probe 14. When combined with hereinafter described aspects of probe 14 that allow two-dimensional ultrasonic scanning in a plurality of precisely oriented transverse, longitudinal and oblique scanning planes, the six-degree-of-freedom measurement system allows the invention to provide two-dimensional images that are spatially in registration with one another. That is, the location and orientation of each scanning plane is known with a high degree of precision in terms of the Cartesian coordinate system that is defined by magnetic field generator 20. Precise registration between the two dimensional images allows greatly improved three-dimensional computer-based reconstruction of a scanned heart or other organ. As is known in the art, three-dimensional cardiac imaging is of growing interest and application relative to hemodynamic monitoring of cardiac function during surgery and postoperative periods as well as for the detection and diagnosis of abnormalities in global or regional myocardial function and cardiac motion.

The ultrasonic imaging arrangement of FIG. 1 provides additional imaging capabilities through the use of a hand-held pointer 28 and a hand-held ultrasonic probe 30. Hand-held pointer 28 includes an electromagnetic sensor of the type described relative to ultrasonic probe 14 of endoscope 10. As is indicated in FIG. 1, hand-held pointer 28 is connected to electronics unit 22 so as to provide personal computer 24 with signals representative of the position and orientation of hand-held pointer 28. In practice, hand-held pointer 28 allows three-dimensional identification or "marking" of various anatomical features such as the location of the mid-line of patient 12, various surface contours of the patient's chest, nipples, umbilicus, etc. Since the electromagnetic sensor of hand-held pointer 28 is subject to the same electromagnetic fields as the electromagnetic sensor of probe 14 (i.e., receives the dipole magnetic fields provided by magnetic field generator 20), the position and orientation of hand-held pointer 28 is in spatial registration with the ultrasonic images provided by probe 14, thus allowing three-dimensional cardiac imaging in which imaged regions of the heart are shown in proper orientation relative to anatomical reference points.

Hand-held ultrasonic probe 30 in FIG. 1 is of conventional configuration, including a transducer of the linear array, phased array or mechanically scanned variety, which further includes an electromagnetic sensor of the previously described type. When connected to electronics unit 22 in the manner shown in FIG. 1, hand-held ultrasonic probe 30 can be used to produce additional two-dimensional images that can be employed with the interlumenally generated images that are provided by probe 14 of ultrasonic endoscope 10. Combining the external ultrasonic imaging of hand-held ultrasonic probe 30 with the transesophageal or transgastric ultrasonic imaging provided by ultrasonic endoscope 10 in effect capitalizes on the respective advantages of internal and external imaging and can result in increased accuracy, image clarity, and more encompassing three-dimensional cardiac images.

Figure 2:
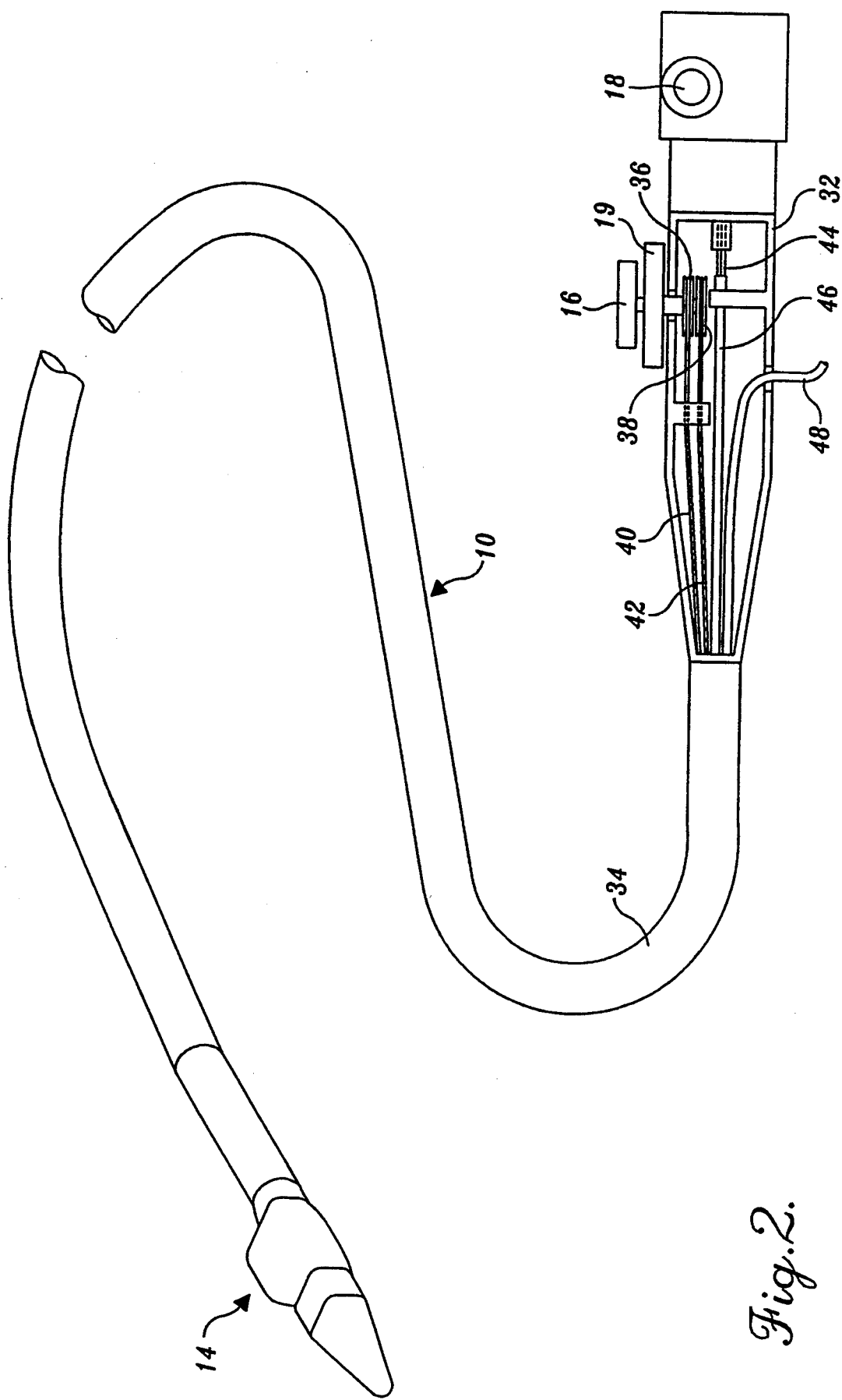
FIG. 2 is a partially cut away perspective view of an ultrasonic endoscope that is configured in accordance with the invention.

In the currently preferred embodiments of the invention, the portion of ultrasonic endoscope 10 that extends through the patient's throat and esophagus and interconnects with ultrasonic probe 14 structurally corresponds to conventional endoscopes. For example, the currently preferred embodiments of the invention utilize the control handle and flexible shaft sections (i.e., an endoscope "shell") that is manufactured by ACMI Corporation of Stamford, Conn. As is indicated in FIG. 2, the handle portion (proximal region) of the depicted ultrasonic endoscope 10 is substantially circular in cross section and is tapered to join with a relatively small diameter endoscope shaft 34, which is flexible and extends between handle 32 and ultrasonic probe 14. Although sufficiently flexible to allow passage along the curved pathway defined by a patient's throat and esophagus, endoscope shaft 34 preferably exhibits a relatively high degree of torsional rigidity (i.e., rotation of handle 32 causes a substantially identical amount of rotation of the end of endoscope shaft 34 that is joined to ultrasonic probe 14). As shall be described hereinafter, ultrasonic probe 14 is also structured for torsional rigidity, thereby allowing probe 14 to be positioned at a desired location in a patient's esophagus or stomach (e.g., behind the left atrium or left ventricle). Although structured for torsional rigidity, ultrasonic probe 14 includes the previously mentioned proximal flexible region, thereby allowing probe 14 to be positioned in firm contact with the wall of the patient's esophagus or stomach.

In the arrangement shown in FIG. 2, the previously mentioned control knob 19 for controlling flexure of ultrasonic probe 14 is mounted concentrically with control knob 16 (which, as previously mentioned, controls rotation of the scanning pattern produced by probe 14 about one of two orthogonal axes). Mounted to the interior end of the shaft on which control knob 19 is mounted is a drive pulley 36. Mounted to the interior end of the shaft of control knob 16 is a similarly sized drive pulley 38. Encircling drive pulleys 36 and 38 are small diameter wires (or, alternatively, inelastic strings or cables) 40 and 42, respectively, which pass along the interior of handle 32 and through the central portion of endoscope shaft 34. As shall be described relative to FIGS. 4–7, wire 40 controls flexure of the proximal region of ultrasonic probe 14. As shall be described relative to FIG. 8, wire 42 controls rotation of the probe 14 scanning plane about an axis that is substantially perpendicular to the longitudinal centerline of endoscope shaft 34 (and hence the longitudinal axis of probe 14).

With continued reference to FIG. 2, control knob 18, which controls rotation of the ultrasonic scanning plane produced by ultrasonic probe 14 about a second orthogonal axis extends outwardly from the rear portion of handle 32. Located within the interior of handle 32 is a 90 degree drive unit (not shown in FIG. 2), which couples control knob 18 to a small diameter flexible shaft 44. In the currently preferred embodiments the drive unit is a 1:5 speed reducer sold by Stock Drive Products of New Hyde Park, N.Y. and identified by part number A2Z23-25R0508. As can be seen in FIG. 2, flexible shaft 44, which is driven by the drive unit, extends longitudinally through the central opening of handle 32 and endoscope shaft 34 passing coaxially through a flexible tube 46. As shall be described relative to FIG. 9, operation of control knob 18 (and hence, rotation of flexible shaft 44) rotates the ultrasonic transducers of ultrasonic probe 14 in a manner that tilts the ultrasonic scanning pattern toward or away from the distal end of ultrasonic probe 14, i.e., "rocks" the ultrasonic scanning pattern about an axis that is orthogonal to the longitudinal axis of ultrasonic probe 14.

Also extending longitudinally along endoscope shaft 34 and through the hollow central portion of handle 32 is an electrical cable assembly 48 (FIG. 2). Electrical cable assembly 48 extends outwardly through handle 32 and includes microcoaxial cables and conventional wires necessary for transmitting electrical signals to and from ultrasonic probe 14. In addition, electrical cable assembly 48 includes conductors which carry the position and orientation signals provided by the electromagnetic sensor of ultrasonic probe 14. As is indicated in FIG. 1, the conductors carrying the position and orientation signals are routed to electronics unit 22. It will be recognized by those skilled in the art that the microcoaxial cables and other conductors that transmit signals to and from ultrasonic probe 14 for purposes of obtaining ultrasonic images are directed to conventional arrangements (not shown in FIG. 1) for producing excitation signals for probe 14 and analyzing and/or storing signals representative of the ultrasonic images obtained.

FIG. 3 generally depicts the exterior features of ultrasonic probe 14 and, in addition, illustrates rotation of the probe scanning pattern about two orthogonal axes 66 and 70, both of which extend orthogonally from longitudinal centerline 62 of probe 14. As can be seen in FIG. 3, the exterior of the configuration of ultrasonic probe 14 is established by a tapered tip 50 that gradually increases in circular cross section and is smoothly joined with an elastomeric sheath 52. Elastomeric sheath 52 is transparent to acoustic energy and surrounds an assembly 53 that includes the ultrasonic transducer array, an arrangement by which the invention rotates the probe scanning pattern about orthogonal axes 66 and 70. Extending rearwardly from acoustically transparent elastomeric sheath 52 is a probe flexure region 54 which joins ultrasonic probe 14 with endoscope shaft 34 (shown in FIG. 2).

All external surfaces of ultrasonic probe 14 and endoscope shaft 34 are biocompatible for human use and impervious to body fluids. In the currently preferred embodiments of ultrasonic probe 14, tapered tip 50 is molded of a relatively pliant elastomeric material such as material identified as product number PMC 724 that is available from Smooth-On Incorporated, Gillette, N.J. If desired or necessary, in order to provide a high degree of resistance to infusion of body fluids and/or superior sterilization capability, a suitable conformal coating can be applied to the outer surface of tapered tip 50. In any case, in the currently preferred embodiments, tapered tip 50 encapsulates an electromagnetic sensor 56 of the type described relative to FIG. 1, with electromagnetic sensor 56 being located near the boundary between tapered tip 50 and acoustically transparent sheath 52. A microphone 58, which serves as a phonocardiogram pick up also is encapsulated in tapered tip 50 being located adjacent forward face of electromagnetic sensor 56. Microphone 58 supplies electrical signals representative of heart sounds thereby allowing a determination of cardiac timing (i.e., temporal identification of events in the cardiac cycle) in accordance with known techniques such as those disclosed in U.S. Pat. No. 4,546,777, which issued to Groch et al. and is entitled "Heart Sound Detector and Synchronization for Diagnostics." It has been found that a small electret microphone of the type used in applications such as lapel microphones and miniature tape recorders exhibit sufficient low frequency response to allow a determination of cardiac timing and, hence, are suitable for use in the invention.

Regardless of the particular microphone or exact technique employed to determine cardiac timing, the derived timing signals can be used to gate (trigger) the ultrasonic transducer array so that two-dimensional image information is produced at predetermined points during the cardiac cycle. Alternatively, the cardiac timing signals can be used to provide temporal registration between each two-dimensional image that is generated by ultrasonic probe 14 and the cardiac cycle. For example, and of specific importance in three-dimensional ultrasonic imaging, the signals provided by microphone 58 of ultrasonic probe 14 can be processed by either of the two above-mentioned techniques to provide a set of two-dimensional images of the left ventricle under end diastolic and end systolic conditions. End diastolic and end systolic left ventricle volumes can then be estimated by processing the two-dimensional images to obtain three-dimensional end diastolic and end systolic images. The end diastolic and end systolic left ventricle volumes readily yield a measure of stroke volume and ejection fraction, which are useful in diagnosing the location, extent and degree of leftventricular dyssynergy.

Referring still to FIG. 3, cross-sectional geometry of elastomeric sheath 52 exceeds that of both the adjoining portion of tapered tip 50 and the adjoining terminus of probe flexure region 54. More specifically, in the arrangement shown in FIG. 3, the central region of elastomeric sheath 52 is of generally rectangular cross-sectional geometry, with the corner regions being smoothly radiused to facilitate passage of ultrasonic probe 14 along the curved pathway formed by a patient's throat and esophagus. Extending between the central region of elastomeric sheath 52 and its interface with tapered tip 50 is a region that is contoured to form a smooth and gradual transition with tapered tip 50. Similarly, a smoothly contoured transition is formed between the mid-section of acoustically transparent sheath 52 and the outer surface of probe flexure region 54.

As was previously mentioned and as is diagrammatically indicated in FIG. 3, the two-dimensional scanning pattern produced by ultrasonic probe 14 can be rotated about two orthogonal axes so that ultrasonic endoscope 10 provides multi-planar imaging signals. More specifically, illustrated in FIG. 3 is a fan-shape ultrasonic scanning pattern 60, which is shown in a reference position in which the two-dimensional scanning pattern lies in a plane that is defined by coordinate axes 66 and 70 and is substantially perpendicular to the longitudinal axis 62 of ultrasonic probe 14. In practice, when ultrasonic probe 14 is positioned as shown in the arrangement of FIG. 1 and control knobs 16 and 18 are operated to position ultrasonic scanning pattern 60 in the depicted reference position, a two-dimensional substantially transverse cardiac image can be produced. When control knob 16 is operated to rotate ultrasonic scanning pattern 60 about axis 66 (indicated by arrows 64 in FIG. 3), ultrasonic scanning pattern 60 is rotated to be in closer alignment with the long axis of a patient's heart. When control knob 18 of FIGS. 1 and 2 is operated to rotate ultrasonic scanning pattern 60 about axis 70 (indicated by arrows 68 in FIG. 3), scanning pattern 60 is tilted toward (or away from) the distal end of ultrasonic probe 14, i.e., the rounded end of tapered tip 50. Thus, rotation of ultrasonic scanning pattern 60 about scanning axis 70 allows positioning of ultrasonic scanning pattern 60 to obtain multiple transverse images of a patient's heart.

In the currently preferred embodiments of the invention, ultrasonic probe 14 is configured for 90 degrees of scanning plane rotation about each of the scanning plane axes 66 and 70 ($\pm 45°$, relative to the reference position shown in FIG. 3). Although greater rotational capability can be provided, $\pm 45°$ of rotation and tilt (or translation) provides multi-planar scanning capability that is sufficient for full and complete imaging of a patient's heart.

Figure 4:
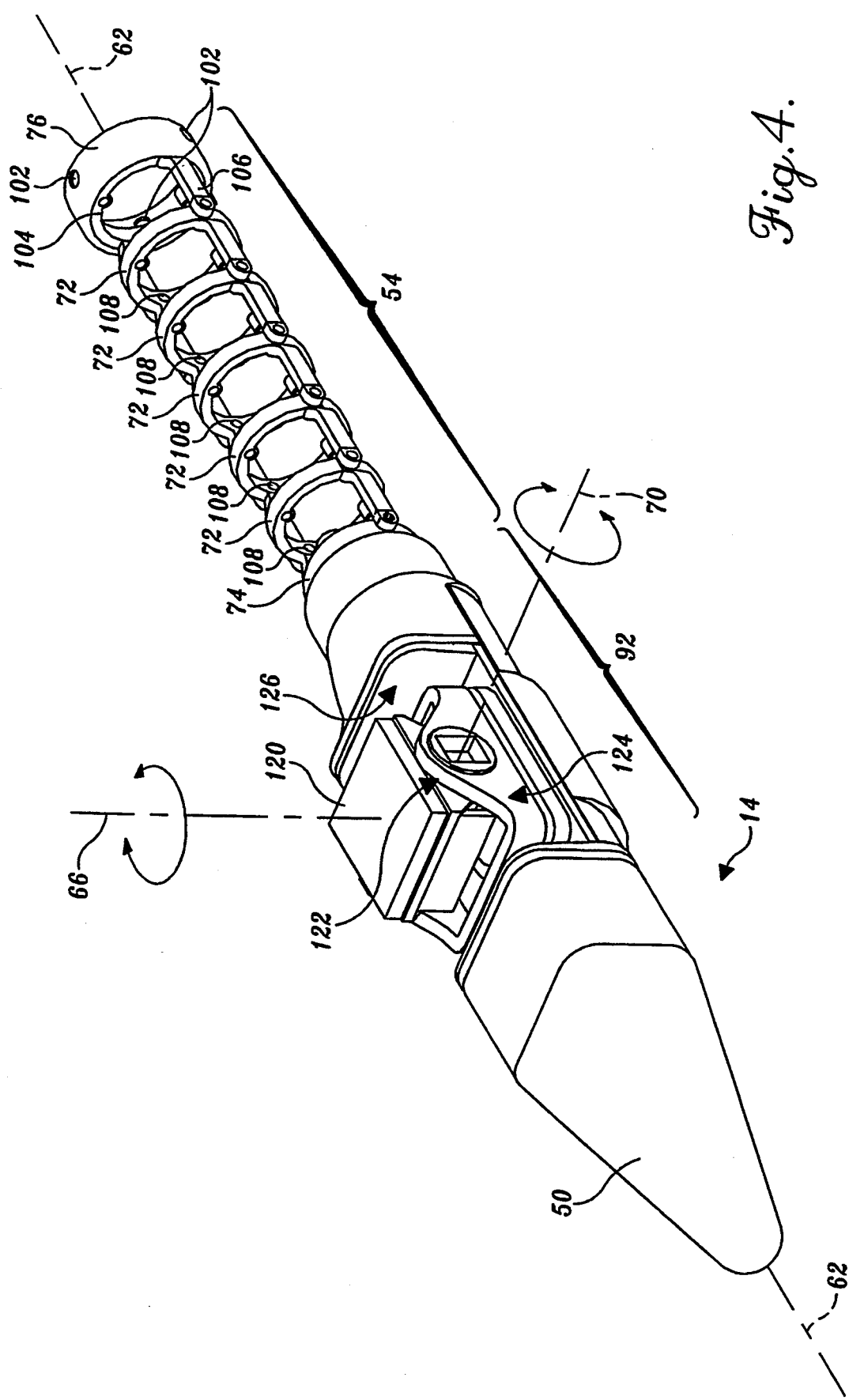
FIG. 4 is a perspective view depicting various portions of the ultrasonic probe of FIG. 3, including a tapered tip, a transducer mounting region that adjoins the tapered tip, and a longitudinally extending probe flexure region that extends from the transducer mounting region.

The structural configuration and operation of probe flexure region 54 that is generally indicated in FIG. 3 can be understood with reference to FIGS. 4-7. As is indicated in FIG. 4, probe flexure region 54 includes a plurality of flexure links 72 that are pivotably interconnected with one another and extend between first and second coupling rings 74 and 76. As can be best seen in FIG. 6, each flexure link 72 includes an annular section 78 and arms 80 that extend orthogonally away from diametrically opposed locations along the cylindrical face of annular section 78. As is indicated in FIG. 4, arms 80 are substantially parallel to one another over the major portion of their length and, in addition, extend in parallel relationship with the longitudinal axis 62 of ultrasonic probe 14. As is shown in both FIGS. 4 and 6, each arm 80 includes a region 82 that is located adjacent to and extends angularly away from annular sections 78 to thereby allow annular section 78 of an adjoining flexure link 72 to be positioned between the outer ends of a pair of arms 80. As can best be seen in FIG. 6, annular section 78 of each flexure link 72 includes a pair of openings 84 that are positioned for alignment with openings 86 in arms 80 when flexure links 72 are assembled with one another. Pins 88 pass freely through openings 86 in arms 80 and are press-fit or otherwise retained in the openings 84 of flexure link annular section 78 to thereby interconnect adjacent flexure links 72 in a manner that allows pivotable movement.

As is indicated in FIG. 4, first coupling ring 74 is pivotably interconnected with the distal-most flexure ring 72 and joins probe flexure region 54 with the portion of ultrasonic probe 14 that houses the probe ultrasonic transducer array and the mechanism (53 in FIG. 3) that provides the previously discussed rotation of the ultrasonic scanning pattern 60 about the two orthogonal axes 66 and 70. More specifically, the portion of ultrasonic probe 14 that houses the transducer assembly (generally indicated in FIGS. 4 and 5 by reference numeral 92), includes an axially cylindrical collar 94 extending toward probe flexure region 54 and coaxially surrounding longitudinal axis 62 of ultrasonic probe 14. As is best shown in FIG. 5, cylindrical collar 94 is configured and dimensioned for installation in a cylindrical recess 96, which is formed at one end of first coupling ring 74. Extending axially from the second end of first coupling ring 74 and concentric with recess 96 is a cylindrical collar 98, the outer diameter of which is substantially identical to the outer diameter of the flexure link annular sections 78. Located in cylindrical collar 98 of first coupling ring 74 is a pair of diametrically opposed circular openings 100, which correspond in size to openings 84 in flexure links 72. As can be seen in both FIGS. 4 and 5, the geometry and configuration of collar 98 of first coupling ring 74 allows first coupling ring 74 to be pivotably interconnected with the distal-most flexure link 72 of probe flexure region 54 in the same manner as adjacent flexure links 72 are pivotably interconnected with one another. That is, openings 86 in the diametrically opposed arms 80 of the distal-most flexure links 72 are aligned with openings 100 in collar 98 and pins (88 in FIG. 6) are securely installed in openings 100 of first coupling ring 74.

Second coupling ring 76 joins probe flexure region 54 to the distal end of endoscope shaft 34, which is shown in FIG. 2. As is illustrated in FIG. 4, second coupling ring 76 includes an axially extending cylindrical recess that is dimensioned for receiving endoscope shaft 34. Circular openings 102, which are circumferentially spaced apart from one another in the wall region of the cylindrical recess permit second coupling ring 76 (and hence ultrasonic probe 14) to be securely joined with endoscope shaft 34 with screws or other fasteners.

Included in second coupling ring 76 and forming the terminal surface of the recess that receives endoscope shaft 34 is an annular flange 104. Pivot arms 106, which are configured and dimensioned to correspond to arms 80 of the flexure links 72 extend outwardly from annular flange 104 of second coupling ring 76. As is shown in FIG. 4, pivot arms 106 are pivotably connected with annular section 78 of the proximal-most flexure link 72 (i.e., the flexure link 72 that is located nearest the terminus of probe flexure region 54).

Figure 6:
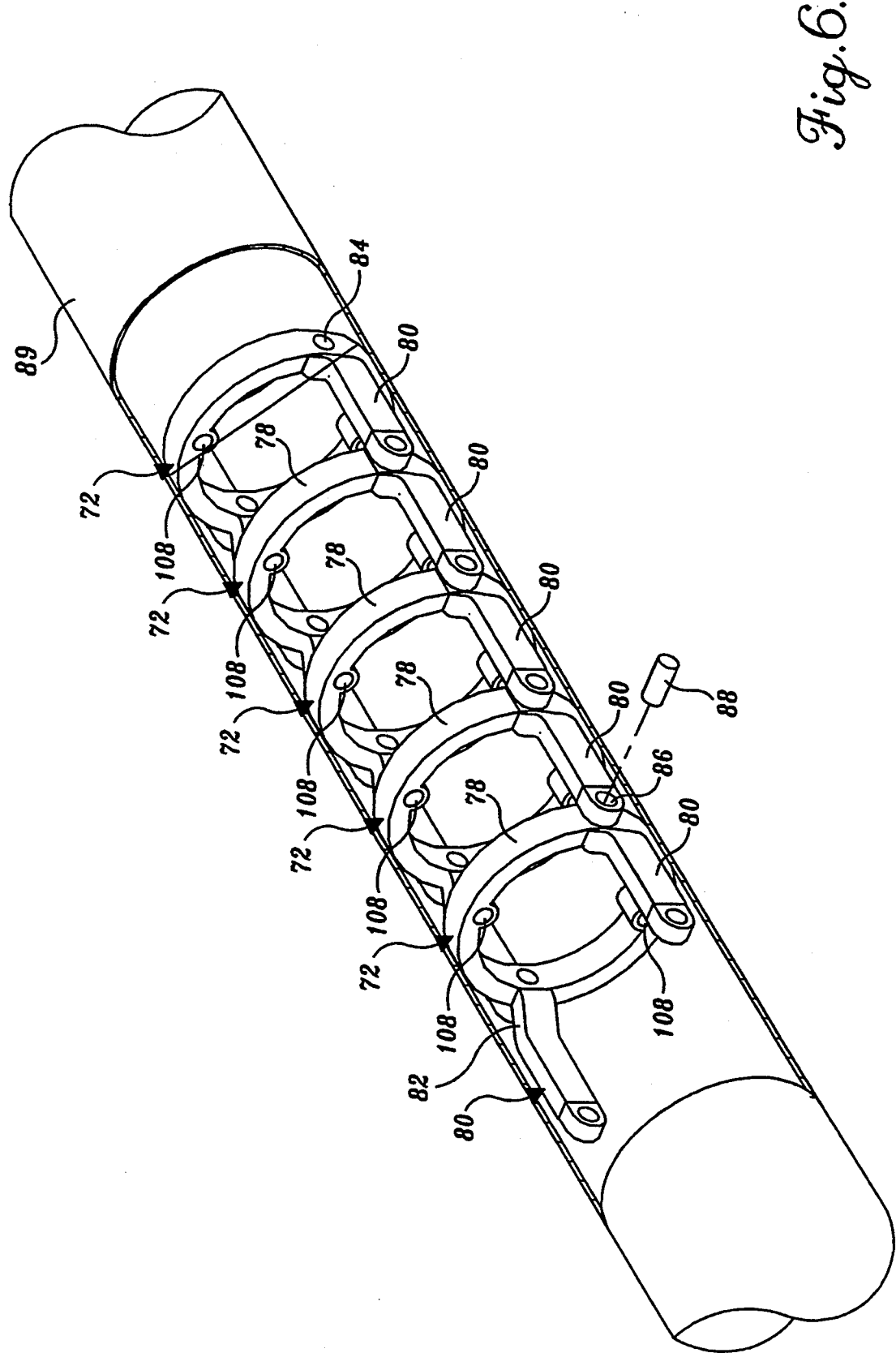
FIG. 6 is a perspective view illustrating the manner in which the probe flexure region of FIG. 4 is structured and arranged.
Figure 7:
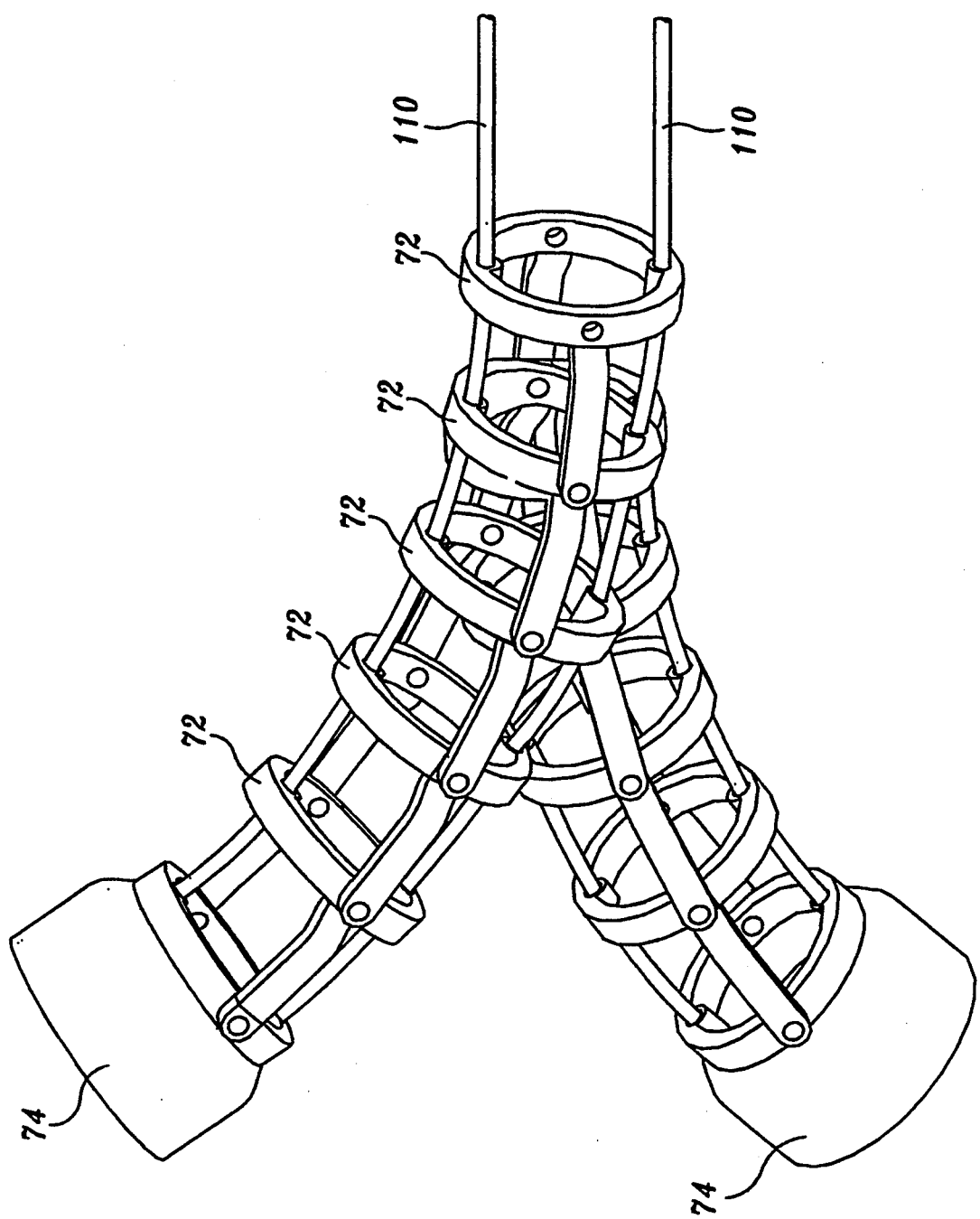
FIG. 7 is a perspective view of the probe flexure region that illustrates the manner in which flexure is achieved.

With reference to FIGS. 4 and 6, annular flange 104 of second coupling ring 76 and annular section 78 of each flexure ring 72 includes a pair of diametrically opposed openings 108, with each opening 108 being positioned midway between the probe flexure region pivot arms (i.e., arms 80 of flexure links 72 and arms 106 of second coupling ring 76). As can be seen in both FIGS. 4 and 6, openings 108 lie in a common plane when probe flexure region 54 is structured and assembled in the above described manner. As is shown in FIG. 7, openings 108 in effect form two spaced apart guides for pull wires 110 which pass through the interior of endoscope shaft 34 from handle 32 of ultrasonic endoscope 10 and are securely attached to first coupling ring 74. When the controls of endoscope 10 are configured in the manner shown in FIG. 2, pull wires 110 correspond to wire 40, which encircles pulley 38 in the endoscope control handle. Thus, in that particular control arrangement, rotating control knob 19 will place one of the pull wires 110 in FIG. 7 under tension, while releasing tension in the other pull wire 110.

As is shown in FIG. 7, activation of pull wires 110 in this manner causes pivoting of adjacent flexure links 72 about pins 88. The pivoting action of adjacent flexure links 72 in turn causes bending (curvature) of probe flexure region 54 in a direction that is determined by the pull string 110 that is placed under tension. In particular, and with reference to the orientation of flexure region 54 that is shown in FIG. 7, when the lower most pull string is placed under tension and tension is relieved in the upper most pull string, the assembled flexure rings 72 cause flexure region 54 of ultrasonic probe 14 to smoothly curve downwardly. On the other hand, when the upper most pull string 110 of FIG. 7 is placed under tension and tension is released in the lower most pull string 110, probe flexure region 54 is curved upwardly.

The above-described structural arrangement of probe flexure region 54 provides at least two important operational features. First, although controlled flexure is provided in a plane that is defined by openings 108 of flexure links 72 of probe 14 (FIGS. 6 and 7), torsional forces caused by rotation of endoscope 10 are transferred between endoscope shaft 34 and first coupling ring 74 (and, hence, the ultrasonic scanning array) without slippage. This torsional rigidity allows precise positioning of the ultrasonic scanning pattern 60 produced by ultrasonic probe 14 with respect to rotation within a patient's esophagus (or stomach). That is, the centerline of the two-dimensional scanning pattern produced by probe 14 can be precisely positioned relative to the long axis of a patient's heart.

The second important operational and functional aspect of the above-described probe flexure region 54 is the ability to in effect tilt ultrasonic probe 14 to thereby ensure gentle but firm contact between the portion of ultrasonic probe 14 that emits ultrasonic energy and a patient's esophagus. Firm but gentle contact is important from the standpoint of positioning and maintaining ultrasonic probe 14 in a desired position throughout a desired interval of ultrasonic scanning. Urging probe 14 into contact with the esophagus also is advantageous from the standpoint of obtaining high quality images since a uniform probe/esophagus interface normally is established.

The structural arrangement for mounting the ultrasonic transducer array and rotating the scanning pattern produced by the array (60 in FIG. 3) about coordinate axes 66 and 70 will now be described with reference to FIGS. 4, 5, 8, and 9. As shall be recognized upon understanding the structure depicted in the figures, the transducer assembly of ultrasonic probe 14 (which is generally indicated in FIG. 3 by reference numeral 53) includes: an ultrasonic transducer array 120; an array holder 122 to which ultrasonic array 120 mounts; a gimbal mount 124, which is configured for rotation of array holder 122 (and hence ultrasonic transducer array 120) about coordinate axis 70 in FIG. 4; and a housing unit 126, which, in combination with acoustically transparent sheath 52 houses the electrical and mechanical components of the ultrasonic scanning assembly. As is best seen in FIGS. 5 and 9, gimbal mount 124 includes a downwardly extending cylindrical shaft 128 which passes through a circular opening in a baseplate 130 of housing unit 126. When shaft 128 is rotated in the hereinafter described manner, ultrasonic transducer array 120 (and, thus, the associated ultrasonic scanning pattern 60 in FIG. 3) is rotated about the previously described coordinate axis 66 (shown in FIGS. 3, 4, and 9).

Ultrasonic transducer array 120 of the currently preferred embodiment of the invention is a 48 element, 4.8 megahertz type TE transducer unit, which is manufactured by Echo Ultrasound of Reedsville, Pa., U.S.A. As can best be seen in FIG. 5, the currently preferred ultrasonic transducer array 120 includes a substantially rectangular upper plate 132 which contains the individual transducers of the array, and two parallel, spaced-apart downwardly extending rectangular flanges 134.

With continued reference to FIG. 5, the upper surface of the depicted array holder 122 is configured to form a rectangular frame that is sized for receiving the downwardly extending flanges 134 of ultrasonic transducer array 120. More specifically, array holder 122 includes two parallel spaced-apart strips 136 that extend between corner regions of two downwardly extending side panels 138 that are substantially triangular in geometry. Extending outwardly from the side panels 138 of array holder 122 are circular pivot shafts 139 that allow rotation of array holder 122 (and hence ultrasonic transducer array 120 about an axis that is parallel to upper plate 132 (and coordinate axis 70 of FIGS. 3, 4 and 8). In the depicted arrangement, pivot shafts 139 of array holder 122 extend through circular openings 140 in upwardly extending parallel walls 142 of gimbal mount 124 to allow rotation in the manner described above (i.e., rotation of transducer array 120 about coordinate axis 70 of ultrasonic probe 14).

As previously mentioned, extending downwardly from the base of gimbal mount 124 is a cylindrical shaft 128 that passes through baseplate 130 of housing unit 126 to thereby allow rotation of ultrasonic transducer array 120 about coordinate axis 66 in FIGS. 3, 4, and 9. As is indicated in the exploded view of FIG. 5, cylindrical shaft 128 passes through a circular opening 144 that is located in the central region of a seal 146. As also is indicated in the exploded view of FIG. 5, seal 146 is installed in a recess 148 of geometry substantially identical to the geometry of seal 146. Tabular regions 150 that are formed in seal 128 and extend away from seal opening 144 prevent seal 146 from rotation in recess 148, and, thus, prevent rotation of seal 148 with rotation of gimbal mount 124 (and hence ultrasonic transducer array 120). Seal 146 prevents acoustic coupling fluid or gel (not specifically shown in the figures) from passing through baseplate 130 of housing unit 126. More specifically, in the depicted arrangement, housing unit 126 in effect partitions the transducer region of ultrasonic probe 16 into upper and lower compartment-like regions. As can be ascertained from FIG. 5, the upper region is defined by housing unit baseplate 130, parallel walls 152 that extend orthogonally upward from baseplate 130, and elastomeric sheath 52, which forms the outer surface of the mid-section (transducer array region) of ultrasonic probe 14. Extending about the edge of each housing unit wall 152 is a groove 154 which receives a corresponding edge region of elastomeric sheath 52. Preferably, these edge regions of elastomeric sheath 52 are formed with peripherally extending beads that project into grooves 154. Regardless of the exact configuration employed, grooves 154 allow a fluid-tight juncture to be formed between housing unit 126 and elastomeric sheath 52 through use of an adhesive and/or a tension band (e.g., string, wire, etc.) that forms elastomeric sheath 52 into grooves 154.

As was indicated in describing seal 146 of FIG. 5, acoustic coupling fluid or gel fills the compartment-like region defined between the upper surface of housing unit baseplate 130 and elastomeric sheath 52. To prevent the acoustic coupling fluid or gel from passing downwardly through the open central region of array holder 22 and the central opening of cylindrical shaft 128 of gimbal mount 124, the currently preferred embodiments of the invention include an elastomeric bellows 158. As can be seen in FIG. 5, bellows 158 includes downwardly extending side panels that are configured to snugly encompass the base region of gimbal mount 124. One or more grooves 160 that extend around the base region of gimbal mount 124 are provided for forming a fluid-tight seal between the downwardly extending walls of bellows 158 and the exterior portion of gimbal mount 124 that is contacted by bellows 158. In the currently preferred embodiments the interior surface of the downwardly extending bellows walls 158 includes a bead (not shown in FIG. 5) which is received by grooves 160. In addition, bellows 158 can be joined to gimbal mount 124 in the same manner as elastomeric sheath 52 is jointed to gimbal mount 124 (e.g., by means of an adhesive sealant and/or by banding the installed bellows 158 so that the elastomeric material forming downwardly extending side panels of bellows 158 is forced into groove 160).

As also is shown in FIG. 5, a rectangular opening 164 is formed in the upper portion of elastomeric bellows 158. When bellows 158 is secured to gimbal mount 124, the edges of array holder 122 are bonded to adjacent portions of bellows 158 by means of a suitable adhesive or other appropriate technique. Ultrasonic transducer array 120 is then installed within rectangular opening 164. As also is shown in FIG. 5, the upper portion of elastomeric bellows 158 includes a series of fan-like folds 166 that extend peripherally around bellows 158. Fan-like folds 166 are sufficient in number and configuration to allow the previously discussed rotation of ultrasonic transducer array 120 about the orthogonal axes 66 and 70 (shown in FIGS. 3, 4, and 9), which, in the currently preferred embodiments of the invention is ±45° relative to axes 66 and 70. Both bellows 158 and elastomeric sheath 52 of the currently preferred embodiments are formed by dipping or otherwise coating suitably shaped molds with a thin layer of uncured synthetic material. One such material marketed under the product name Tactylon 453 (15% solids) and supplied by Tactylon Technologies of Vista, Calif. has been used to form bellows and sheath wall thicknesses on the order of 0.005 inch.

Figure 8:
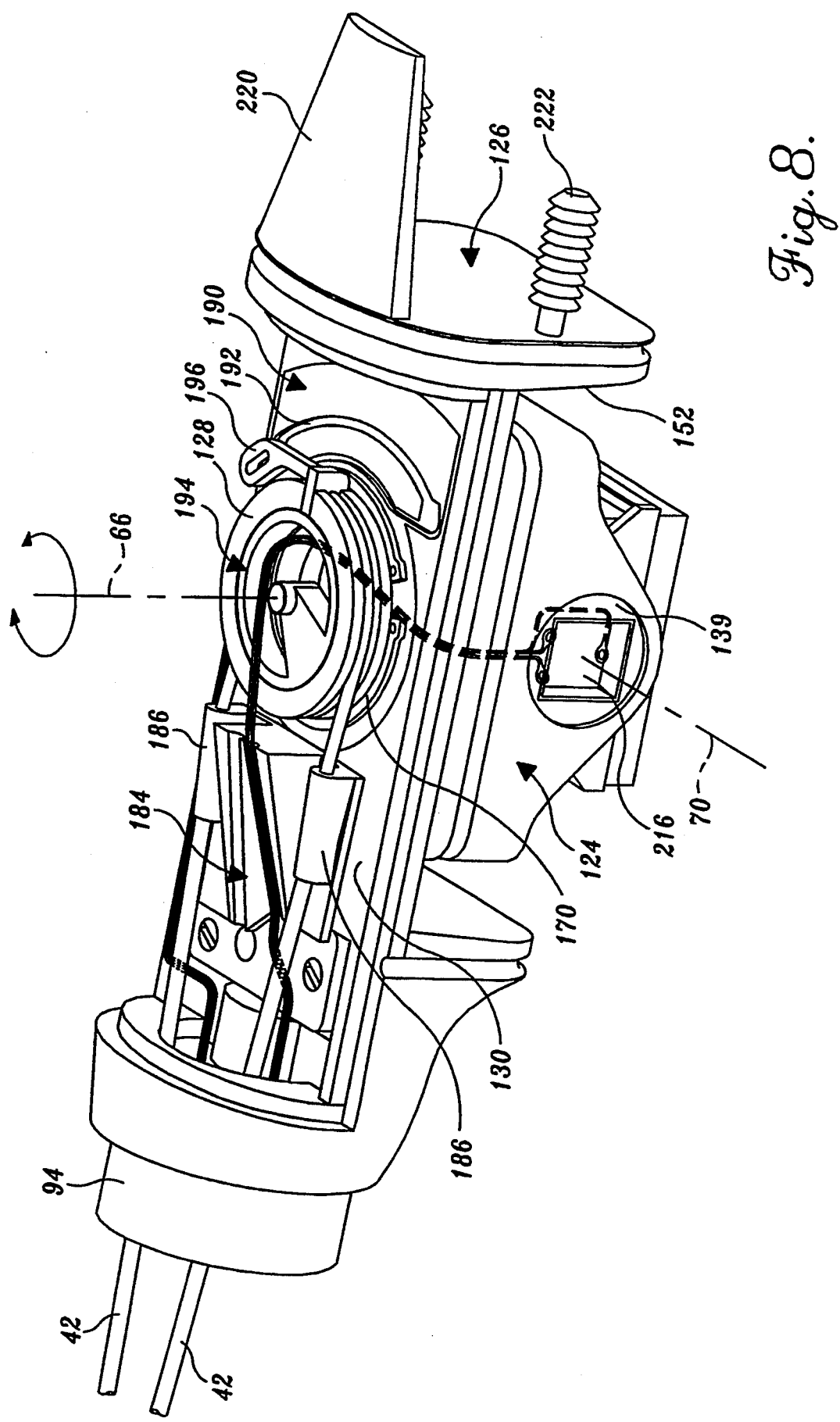
FIG. 8 is a perspective view of a portion of the transducer assembly shown in FIGS. 4 and 5 and depicts the manner in which rotation about one orthogonal axis can be achieved.
Figure 9:
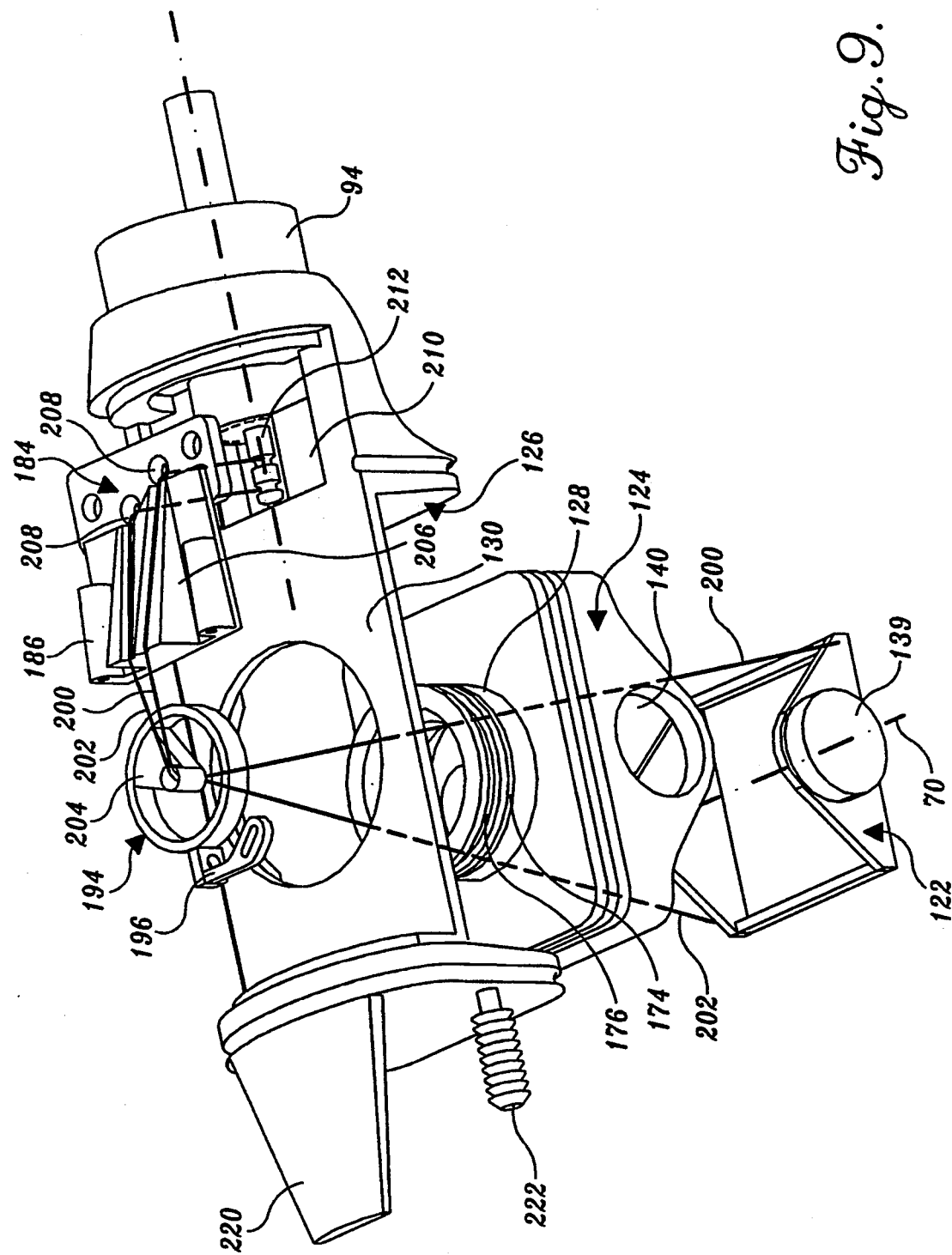
FIG. 9 is an exploded view a portion of the transducer assembly of FIGS. 4 and 5 and depicts the manner in which rotation about the second orthogonal axis can be achieved.

As can be recognized in view of FIGS. 5, 8, and 9, the compartment-like region that is formed on the opposite side of baseplate 130 of housing unit 126 (i.e., a lower compartment-like region when probe 14 is oriented as shown in FIG. 5), extends from the distal-most wall 152 of housing unit 126 to the portion of housing unit 126 that forms collar 94. As stated in describing probe flexure region 54, collar 94 mates with and is fastened to first coupling ring 74 to thereby join probe flexure region 54 to the remaining structure of ultrasonic probe 14. As also can be ascertained from FIGS. 5, 8, and 9, the lower boundary of the compartment-like region is formed by a longitudinally extending cover plate 170 that is of arcuate cross-sectional geometry. As is indicated in FIGS. 4 and 5, cover plate 170 mates with and is fastened to the lower portion of housing unit 126.

As was previously described and as can be seen most clearly in FIG. 8, the end region of cylindrical shaft 128 of gimbal mount 124 extends through baseplate 130 of housing unit 126 (i.e., through seal 146 in FIG. 5). Extending circumferentially about the outer wall of cylindrical shaft 128 are two spaced-apart grooves 174 and 176 (shown most clearly in FIG. 9). As is indicated in FIG. 8, a compression type retainer ring 170 is installed in groove 174 to maintain cylindrical shaft 128 (and hence gimbal 124) assembled with housing unit 126. As also is shown in FIG. 8, wire 42, which is driven by endoscope control knob 16 of FIG. 2, is installed in groove 174 of cylindrical shaft 128. More specifically, in the depicted arrangement, wire 42 (which extends through the central opening of endoscope shaft 34), passes through the central opening of collar 94 of housing unit 126 and is looped about cylindrical shaft 128 of gimbal 124 (i.e., is engaged with groove 176). Positioned between cylindrical shaft 128 of gimbal 124 and collar 94 of housing unit 126 is a guide fixture 184 that is formed in or secured to baseplate 130 of housing unit 126. Included in guide fixture 184 are two substantially parallel elongate upwardly extending projections 186. Elongate projections 186 of guide fixture 184 serve as guides for wire 42, with wire 42 passing through circular openings that extend longitudinally through projections 186.

In view of the structural arrangement depicted in FIG. 9, it can be recognized that gimbal 124, array holder 122 and ultrasonic transducer array 120 can be rotated about axis 66 by moving wire 42 to cause rotation of cylindrical shaft 128. With respect to the arrangement of endoscope 10 that is depicted in FIG. 2, it can be recognized that the necessary movement of wire 42 can be obtained by rotating control knob 16 which is linked to and rotates pulley 38. It also can be recognized that various other "pull-string" arrangements can be employed to cause rotation of cylindrical shaft 128 to thereby rotate ultrasonic transducer array (and the ultrasonic scanning pattern produced by the array) about axis 66 in FIG. 8.

As was described relative to FIG. 1, the electromagnetic sensor of ultrasonic probe 14 (electromagnetic sensor 56 in FIGS. 3 and 4) operates in conjunction with a magnetic field generator 20 to provide signals representative of the position and orientation of the electromagnetic sensor relative to a three-dimensional coordinate system that is established by (referenced to) the magnetic field generator. Thus, electromagnetic sensor 56 provides signals representative of the position and orientation of ultrasonic probe 14 with respect to the three-dimensional coordinate system established by the magnetic field generator. However, what is required in most situations is the position and orientation of the ultrasonic scanning pattern (60 in FIG. 3).

As previously described, in the practice of the invention, the ultrasonic scanning pattern 60 (in FIG. 3) is rotatable about two orthogonal axes 66 and 70 (in FIGS. 3, 4, 8 and 9). As can be readily seen from the figures, the position(s) of axes 66 and 70 are fixed in space relative to the position of electromagnetic sensor 56. Thus, the origin of the two-dimensional coordinate system defined by axes 66 and 68 can be determined relative to the three-dimensional space defined by magnetic field generator 20 of FIG. 1 by conventional coordinate translation techniques. The orientation of ultrasonic scanning pattern 60 in the three-dimensional coordinate system defined by magnetic field generator 20 can then be determined based on the amount ultrasonic scanning pattern 60 is rotated about axes 66 and 70 (i.e., by the amount that control wire 42 rotates gimbal mount 124 (shown in FIG. 8) and by the amount ultrasonic transducer array 120 is tilted toward or away from longitudinal axis 62 of ultrasonic probe 14 (shown in FIG. 4)).

In the currently preferred practice of the invention, an indication of the rotational position of gimbal mount 124 relative to axis 66 (and hence the rotation of ultrasonic scanning pattern 60 about axis 66) is provided by a potentiometer, which is identified in FIG. 8 by reference numeral 190. Although various types of potentiometers can be used (as well as other position sensing techniques), potentiometer 190 of the currently preferred embodiments is a commercially available component that is sold by Mouser Electronics of Gilroy, Calif. and is identified by part number 31VC401.

As can be seen in FIG. 8, potentiometer 190 is of planar geometry and is mounted to plate 130 of housing unit 126. A wiper track 192 extends across the surface of potentiometer 190 in spaced apart parallel relationship with the outer circumference of cylindrical shaft 128. A guide ring 194 is press fit or otherwise retained within the terminal region of the central opening of cylindrical shaft 128. Guide ring 194 includes an actuator arm 196, which extends outwardly through a recess of cylindrical shaft 128 and which pivotably interconnects with the wiper arm of potentiometer 190. In this arrangement, when cylindrical shaft 128 (and, hence, the ultrasonic scanning pattern produced by ultrasonic probe 14 is rotated by movement of control wires 42, actuator arm 196 moves the wiper arm of potentiometer 190 along wiper track 192). Thus, the resistance potentiometer 190 (as measured between the potentiometer wiper contact and either end of the potentiometer) provides an indication of the rotational position of gimbal mount 124 (and hence ultrasonic scanning pattern 160 of FIG. 3) relative to axis of rotation 66. As noted above, this measurement of rotational position is required in order to determine the position of ultrasonic scanning pattern 60 relative to the three-dimensional coordinate system defined by magnetic field generator 20 of FIG. 1.

The manner in which the currently preferred embodiments of the invention are configured to rotate ultrasonic scanning pattern 160 about axis 170 (FIG. 3) and provide a signal representative of the rotational position, i.e., amount of tilt relative to the ultrasonic probe longitudinal axis 62, can be understood with reference to FIG. 9 which is shown in exploded view to better illustrate important aspects of the arrangement. In FIG. 9, a pair of pull strings 200 and 202 are connected to diagonally opposite corners of array holder 122, with pull strings 200 and 202 extending through the central opening of gimbal mount cylindrical shaft 128. In exiting cylindrical shaft 128, pull strings 200 and 202 pass through a tubular centering guide 204 that is formed in the central opening of guide ring 194 (which was described relative to FIG. 8). Passing from centering guide 204 of guide ring 194, pull strings 200 and 202 are routed through channel-like recesses in wedge-like projection 206 that forms an upwardly extending inclined surface along the mid-region of guide fixture 184 (described earlier relative to FIG. 8). At the lower terminus of wedge-like projection 206, pull strings 200 and 202 pass downwardly through openings 208 in guide fixture 184. As can be seen in FIG. 9, passage of pull strings 200 and 202 through openings 208 places the pull strings in a recess 210 of housing unit 126, with the recess 210 being spaced apart from cylindrical collar 94. Extending axially along recess 210 is a rotatable shaft 212, which passes through a bearing 213 and includes a pair of spaced apart circumferential grooves. Pull strings 200 and 202 are wound in the grooves of rotatable shaft 212, with one of the pull strings being wound in a clockwise direction and the other pull string being wound in a counter clockwise direction. Thus, when shaft 212 is rotated, one of the pull strings 200 and 202 will unwind from shaft 212 and the other pull string will be wound onto shaft 212. Accordingly, depending upon the direction of rotation, array holder 122 will tilt toward or away from ultrasonic probe longitudinal axis 62. That is, array holder and, hence, ultrasonic scanning pattern 160 of FIG. 3 will rotate about coordinate axis 70 of FIGS. 3, 4, 8 and 9. In the currently preferred embodiments of ultrasonic probe 14, shaft 212 is coupled to and driven by flexible shaft 44 of endoscope 10 (both described relative to FIGS. 1 and 2).

The rotational position of ultrasonic scanning pattern 160 relative to axis 70 is provided by a potentiometer that is mounted and arranged to provide a resistance value indicative of the angular rotation of array holder 122 about axis 70. FIG. 8 illustrates a suitably configured and mounted potentiometer 216, which is of rectangular geometry and is mounted in a recess in the central portion of one of the pivot shafts 139 that extend outwardly from array holder 122 to pivotally interconnect array holder 122 with gimbal mount 124. In this arrangement, the wiper arm of potentiometer 216 is secured to gimbal mount 24 so that the wiper arm of the potentiometer moves along a wiper track when array holder 122 tilts, thereby providing a resistance value indicative of the rotational position of array holder 122 relative to gimbal mount 124 and hence, the rotational position of ultrasonic scanning pattern 60 relative to axis 66 (FIG. 3). One commercially available potentiometer suitable for use as potentiometer 216 is available from Rohm Corporation of Irvine, Calif. and is identified by part number MVR 32.

As was described earlier, tapered tip 50 of ultrasonic probe 14 is molded of an elastomeric material and encapsulates electromagnetic sensor 56. As is shown in FIGS. 5 and 8, the currently preferred embodiments of the invention include provision for mounting of electromagnetic sensor 56 and secure retainment of tapered tip 50. In particular, extending forwardly from wall 152 of housing unit 126 is a shelf-like projection 220 for supporting electromagnetic sensor 56. Also projecting forwardly from wall 152 is a circular post 222 which includes a series of circumferentially extending rings or ridges. During manufacture of the embodiment of ultrasonic probe 14 that is shown in the figures, electromagnetic sensor 56 is fastened to shelf-like projection 220 and microphone 58 is positioned on the forward face of electromagnetic sensor 56. A mold cavity that corresponds to the desired configuration of tapered tip 50 is filled with uncured elastomeric material and the partially assembled housing unit is placed over the mold cavity with microphone 58, electromagnetic sensor 56 and post 222 extending downwardly into the cavity. When the elastomeric material has cured to form tapered tip 50, the partially assembled housing unit 26 and securely attached tapered tip 50 are withdrawn from the mold.

In view of the foregoing description of the currently preferred embodiments of ultrasonic probe 14, it will be recognized that the number of electrical conductors that must be routed through the probe is relatively high in view of the small cross-sectional size of ultrasonic probe 14. For example, the previously described embodiment of the invention employs an ultrasonic transducer array (120 in FIG. 5) that includes 48 transducer elements and requires on the order of 65 electrical connections and, hence, electrical conductors. To provide the necessary electrical connections while maintaining minimum probe cross-sectional profile, the currently preferred embodiments of the invention employ miniature ribbon-like dynamic flex circuits in which rolled annealed copper conductors that are 2/1000 inch thick and 5/1000 inch wide are spaced apart from one another by 5/1000 inch and bonded between two layers of 1/1000 inch thick polyimide film. This arrangement is illustrated in FIG. 8 with the ribbon-like flex circuits being identified by reference numeral 224. Interconnection of the individual conductors of the flex circuits 224 with the previously mentioned microcoaxial cables and other conductors that extend through endoscope shaft 34 (i.e., electrical cable 48 of FIG. 2) preferably is made in the interior region of cylindrical collar 94 of housing unit 126.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. Apparatus for multi-planar translumenal ultrasonic scanning, said apparatus comprising:
   (a) An ultrasonic scanning probe; said ultrasonic scanning probe being fixed in position and stationary relative to a first probe coordinate system; said ultrasonic scanning probe including a transducer for generating a two-dimensional ultrasonic scanning pattern and means for rotating said transducer relative to first and second coordinate axes of said first probe coordinate system, said means for rotating said transducer in turn selectively rotating said two-dimensional scanning pattern relative to said first and second coordinate axes of said first probe coordinate system; said ultrasonic scanning probe further including electromagnetic sensor means mounted in a fixed orientation for providing signals responsive to a magnetic field that is generated external of said ultrasonic scanning probe, said magnetic field defining a second probe coordinate system having an origin that is spaced apart from said probe, said electromagnetic sensor means for providing a signal representative of the position and orientation of said electromagnetic sensor means and said first probe coordinate system relative to said second probe coordinate system;
   (b) An endoscopic shell having a distal end interconnected with said probe and a proximate end that includes a handle, at least a portion of said endoscopic shell that extends between said handle and said distal end being flexible to the extent required for positioning said ultrasonic scanning probe for multi-planar translumenal ultrasonic scanning; and (c) Control means located in said endoscopic shell, said control means being operable for selectively rotating and positioning said ultrasonic scanning pattern about said first and second coordinate axes of said first probe coordinate system.

2. The apparatus for multi-planar translumenal ultrasonic scanning of claim 1 wherein said ultrasonic scanning probe further includes first and second rotational indicators for supplying first and second rotation signals that respectively represent the rotational position of said two-dimensional scanning pattern relative to said first coordinate axis of said first probe coordinate system and the rotational position of said two-dimensional ultrasonic scanning pattern relative to said second coordinate axis of said first probe coordinate system, said first and second rotational signals for use in combination with said signals provided by said electromagnetic sensor means to indicate the position and orientation of said two-dimensional ultrasonic scanning pattern with respect to said second probe coordinate system.

3. The apparatus for multi-planar translumenal ultrasonic scanning of claim 2 wherein the region of said ultrasonic scanning probe that is interconnected with said distal end of said endoscopic shell is configured and arranged for flexure in a single plane and said endoscopic shell further includes control means operable for establishing the degree of flexure.

4. The apparatus for multi-planar translumenal ultrasonic scanning of claim 3 wherein said apparatus is intended for use in cardiac scanning and said ultrasonic scanning probe further includes a microphone for supplying electrical signals representative of heart sounds.

5. The apparatus for multi-planar translumenal ultrasonic scanning of claim 1 wherein said apparatus is intended for ultrasonic scanning of a subject's heart and said origin of said second probe coordinate system is external of the subject.

6. The apparatus for multi-planar translumenal ultrasonic scanning of claim 1 wherein said means for rotating said ultrasonic transducer relative to one axis of said probe coordinate system includes a housing unit having a base region in which is located a circular opening and said means for rotating said ultrasonic transducer relative to said one axis further includes structural support means for mounting of said ultrasonic transducer, said structural support means including a cylindrical shaft that extends through said opening of said housing unit, said cylindrical shaft being rotatable to rotate said ultrasonic transducer and said two-dimensional ultrasonic scanning array about said first axis of said first probe coordinate system.

7. The apparatus for multi-planar translumenal ultrasonic scanning of claim 6 wherein said transducer support structure includes a transducer holder for mounting of said transducer, said transducer holder including at least one pivot shaft for allowing rotation of said transducer holder relative to said second coordinate axis of said first probe coordinate system; and wherein said transducer support mechanism further includes a gimbal mount, said gimbal mount including said cylindrical shaft of said transducer support assembly and further including an opening for receiving each pivot shaft of said transducer holder.

8. The apparatus for multi-planar translumenal ultrasonic scanning of claim 1 wherein the region of said ultrasonic scanning probe that is interconnected with said distal end of said endoscopic shell is configured and arranged for flexure in a single plane and said endoscopic shell further includes control means operable for establishing the degree of flexure.

9. The apparatus for multi-planar translumenal ultrasonic scanning of claim 8 wherein said means for rotating said ultrasonic transducer relative to one axis of said first probe coordinate system includes a housing unit having a base region in which is located a circular opening and said means for rotating said ultrasonic transducer relative to said one axis further includes structural support means for mounting of said ultrasonic transducer, said structural support means including a cylindrical shaft that extends through said opening of said housing unit, said cylindrical shaft being rotatable to rotate said two-dimensional ultrasonic scanning array about said first axis of said first probe coordinate system.

10. The apparatus for multi-planar translumenal ultrasonic scanning of claim 9 wherein said transducer support structure includes a transducer holder for mounting of said transducer, said transducer holder including at least one pivot shaft for allowing rotation of said transducer holder relative to said second coordinate axis of said first probe coordinate system; and wherein said transducer support mechanism further includes a gimbal mount, said gimbal mount including said cylindrical shaft of said transducer support assembly and further including an opening for receiving each pivot shaft of said transducer holder.

11. The apparatus for multi-planar translumenal ultrasonic scanning of claim 10 wherein said ultrasonic scanning probe further includes first and second rotational indicators for supplying first and second rotation signals that respectively represent the rotational position of said two-dimensional scanning pattern relative to said first coordinate axis of said first probe coordinate system and the rotational position of said two-dimensional ultrasonic scanning pattern relative to said second coordinate axis of said first probe coordinate system, said first and second rotational signals for use in combination with said signals provided by said electromagnetic sensor means to indicate the position and orientation of said two-dimensional ultrasonic scanning pattern with respect to said second probe coordinate system.

12. An ultrasonic translumenal scanning system for providing multi-planar images of internal tissue and organs from a single lumenal location within the body of a subject, said ultrasonic translumenal scanning system comprising:

(a) a magnetic field generator located outside the body of the subject, said magnetic field generator for supplying a magnetic field having three orthogonal field components that define a first coordinate system;

(b) an ultrasonic endoscope for lumenal insertion in the body of the subject, said ultrasonic endoscope including an endoscopic shell, a probe mounted to the distal end of said endoscopic shell, and a control handle mounted to the proximate end of said endoscopic shell; said probe including a magnetic field sensor for detecting the magnetic field strength of each of said three orthogonal field components of said magnetic field supplied by said magnetic field generator, said magnetic field sensor for supplying a signal representative of said field strength of each of said three orthogonal field components supplied by said magnetic field generator, said magnetic field sensor being mounted at a fixed position within said probe; said probe further including transducer mounting means and an ultrasonic transducer for generating a two-dimensional ultrasonic scanning pattern, said ultrasonic transducer being mounted to said transducer mounting means with said transducer mounting means being positioned in said probe at a predetermined location relative to said magnetic field sensor, said transducer mounting means including means for rotating said ultrasonic transducer about two orthogonal axes of a second coordinate system in which the first of said two axes lies in the plane of said two-dimensional scanning pattern and the second of said two axes is substantially perpendicular to both said first coordinate axis and the axial center line of said probe; said control handle including first and second manually operable actuators interconnected with said transducer mounting means, said first manually operable actuator being operable for rotating said two-dimensional scanning pattern about said first axis of said second coordinate system, said second manually operable actuator being operable for rotating said two-dimensional scanning pattern about said second axis of said second coordinate system; said probe further including first and second rotational sensors mounted to said transducer mounting, said first rotational sensor for supplying a signal representative of the amount by which said two-dimensional scanning pattern is rotated about said first axis of said second coordinate system, said second rotational sensor for supplying a signal representative of the amount by which said two-dimensional scanning pattern is rotated about said second axis of said coordinate system; and (c) electrical conductors for coupling said signal supplied by said magnetic field sensor and said signals representative of said rotation about said first and second axes of said second coordinate system through said endoscopic shell to a location external of said ultrasonic endoscope, said electrical conductors including conductors also for supplying signals to said ultrasonic transducer for producing said two-dimensional scanning pattern and for supplying imaging signals generated by said ultrasonic transducer to a location external of said ultrasonic endoscope.

13. The ultrasonic translumenal scanning system of claim 12 wherein:

said system further comprises a series of hinged together flexure rings extending between said probe and the distal end of said endoscopic shell, said hinged together flexure rings being operable to impart curvature to the region between said probe and said distal end of said endoscopic shell with said curvature being limited to a single plane; and, wherein said control handle of said ultrasonic endoscope further includes a third manually operable actuator interconnected with said probe for establishing the degree of curvature imparted by said flexure rings to thereby allow said probe to be placed at a selected position and a selected orientation within said lumen of the subject and to be maintained at said selected position and orientation during a period of time in which said first and second manually operable actuators are operable to produce a plurality of two-dimensional images that correspond to different planes through a selected organ of the subject.

14. The ultrasonic translumenal scanning system of claim 13 wherein each said flexure ring includes an annular section and first and second arms that extend orthogonally away from diametrically opposed locations on said annular section, said first and second arms being substantially parallel to one another and being substantially parallel to the axis of said ultrasonic endoscope, the outward end of each first and second arm of a flexure ring being pivotably interconnected with the annular ring of an adjoining flexure ring.

15. The ultrasonic translumenal scanning system of claim 14 wherein said third manually operable actuator includes a drive pulley mounted in said control handle, said drive pulley including a shaft that extends outwardly through said control handle with said shaft being rotatable to rotate said drive pulley, each said flexure ring including first and second diametrically opposed openings extending through said annular ring of said flexure ring with said diametrically opposed openings being equally spaced apart from said arms of said flexure ring, said third manually operable actuator further including a cable that encompasses said drive pulley and extends through said diametrically opposed openings in said flexure rings, the ends of said cable being connected to diametrically opposed positions on the end of said probe that is nearest said control handle, with said diametrically opposed positions on the end of said probe being substantially in line with said diametrically opposed openings in the distal most flexure ring.

16. The ultrasonic translumenal scanning system of claim 12 wherein said transducer mounting means includes a cylindrical shalt extending coaxially about said first axis of said second coordinate system and includes a bearing surface for rotatably receiving said cylindrical shalt to allow rotation of said two-dimensional scanning pattern about said first axis of said second coordinate system, said transducer mounting means further including a gimbaled transducer holder having a gimbal axis substantially orthogonal to said first axis of said second coordinate system and substantially parallel to said second axis of said second coordinate system, said ultrasonic transducer being mounted in said transducer holder with said transducer holder being rotatable about said gimbal axis to rotate said two-dimensional scanning pattern about said second axis of said second coordinate system.

17. The ultrasonic translumenal scanning system of claim 16 wherein said cylindrical shalt of said transducer mounting means extends outwardly through said bearing surface and includes an inwardly extending circumferential groove and wherein said first manually operable actuator includes a first drive pulley located in said control handle and a cable that encircles both said first drive pulley and said circumferential groove of said cylindrical shaft, said first drive pulley being rotatable by a shaft that extends outwardly from said control handle to, in turn, rotate said cylindrical shaft and said two-dimensional scanning pattern about said first axis of said second coordinate system.

18. The ultrasonic translumenal scanning system of claim 17 wherein said second manually operable actuator includes a flexible drive shaft extending through said endoscopic shell from said control handle to said probe, said control handle including an actuator for rotating said flexible drive shaft, the end of said flexible drive shaft that extends to said probe including a pair of spaced-apart grooves that extend radially inward into said shaft and circumferentially around said shaft, said second manually operable actuator further including first and second pull strings, said first pull string being wound in a clockwise direction in one of said grooves with the outward end of said pull string being connected to said gimbaled transducer holder, said second pull string being wound in a counter clockwise direction in the second of said grooves with the outer end of said second pull string being connected to said gimbaled transducer holder, said first and second pull strings rocking said gimbaled transducer holder about said gimbal axis in response to rotation of said flexible drive shaft.

19. The ultrasonic translumenal scanning system of claim 18 wherein:
    said system further comprises a series of hinged together flexure rings extending between said probe and the distal end of said endoscopic shell, said hinged together flexure rings being operable to impart curvature to the region between said probe and said distal end of said endoscopic shell with said curvature being limited to a single plane; and
    wherein said control handle of said ultrasonic endoscope further includes a third manually operable actuator interconnected with said probe for establishing the degree of curvature imparted by said flexure rings to thereby allow said probe to be placed at a selected position and a selected orientation within said lumen of the subject and to be maintained at said selected position and orientation during a period of time in which said first and second manually operable actuators are operable to produce a plurality of two-dimensional images that correspond to different planes through a selected organ of the subject.

20. The ultrasonic translumenal scanning system of claim 19 wherein each said flexure ring includes an annular section and first and second arms that extend orthogonally away from diametrically opposed locations on said annular section, said first and second arms being substantially parallel to one another and being substantially parallel to the axis of said ultrasonic endoscope, the outward end of each first and second arm of a flexure ring being pivotably interconnected with the annular ring of an adjoining flexure ring.

21. The ultrasonic translumenal scanning system of claim 20 wherein said third manually operable actuator includes a second drive pulley mounted in said control handle, said second drive pulley including a shaft that extends outwardly through said control handle with said shaft being rotatable to rotate said drive pulley, each said flexure ring including first and second diametrically opposed openings extending through said annular ring of said flexure ring with said diametrically opposed openings being equally spaced apart from said arms of said flexure ring, said third manually operable actuator further including a cable that encompasses said second drive pulley and extends through said diametrically opposed openings in said flexure rings, the ends of said cable being connected to diametrically opposed positions on the end of said probe that is nearest said control handle, with said diametrically opposed positions on the end of said probe being substantially in line with said diametrically opposed openings in the distal most flexure ring.

* * * * *